US008237005B2

(12) United States Patent
Ban

(10) Patent No.: US 8,237,005 B2

(45) Date of Patent: Aug. 7, 2012

(54) METHOD FOR SEPARATING AND PRODUCING CYCLOHEXENE

(75) Inventor: Masakazu Ban, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 339 days.

(21) Appl. No.: 12/676,250

(22) PCT Filed: Sep. 5, 2007

(86) PCT No.: PCT/JP2007/067330

§ 371 (c)(1),
(2), (4) Date: Mar. 3, 2010

(87) PCT Pub. No.: WO2009/031216

PCT Pub. Date: Mar. 12, 2009

(65) Prior Publication Data

US 2010/0197988 A1 Aug. 5, 2010

(51) Int. Cl.
*C07C 7/08* (2006.01)

(52) U.S. Cl. ......................... 585/809; 585/833; 585/860

(58) Field of Classification Search ......................... None
See application file for complete search history.

(56) References Cited

U.S. PATENT DOCUMENTS

| | | | |
|---|---|---|---|
| 3,702,886 A | 11/1972 | Argauer et al. | |
| 4,372,930 A | 2/1983 | Short et al. | |
| 4,397,825 A | 8/1983 | Whittam | |
| 4,537,757 A | 8/1985 | Chono et al. | |
| 5,069,756 A * | 12/1991 | Berg | 203/51 |
| 5,865,958 A | 2/1999 | Kanda et al. | |
| 5,969,202 A | 10/1999 | Ashida et al. | |

FOREIGN PATENT DOCUMENTS

| | | |
|---|---|---|
| EP | 0 054 386 | 6/1982 |
| EP | 0065 400 | 11/1982 |
| JP | 52-144649 A | 12/1977 |
| JP | 57-3714 A | 1/1982 |
| JP | 57-123817 A | 8/1982 |
| JP | 57-129820 A | 8/1982 |
| JP | 57-200218 A | 12/1982 |
| JP | 58-110419 A | 7/1983 |
| JP | 58-164524 A | 9/1983 |
| JP | 04-041131 B | 11/1983 |
| JP | 59-128210 A | 7/1984 |
| JP | 01-135730 A | 5/1989 |
| JP | 03-193622 A | 8/1991 |
| JP | 09-030994 A | 2/1997 |
| JP | 09-169669 A | 6/1997 |
| JP | 10-279508 A | 10/1998 |
| JP | 11-228472 A | 8/1999 |

OTHER PUBLICATIONS

Vega, Solvent Selection for Cyclohexane-Cyclohexene-Benzene Separation by Extractive Distillation Using Non-Steady-State Gas Chromatography, Ind. Eng. Chem. Res. 36, 803-807, 1997.

Decision to Grant Patent dated Sep. 8, 2011.

Henan Huagong et al., Detection of Dimethylacetamide at the Bottom of a Column of a Cyclohexanol Apparatus 200#, vol. 8, (2002), pp. 37-38.

* cited by examiner

*Primary Examiner* — Tam M Nguyen

(74) *Attorney, Agent, or Firm* — Morgan, Lewis & Bockius LLP

(57) ABSTRACT

There is provided a method for separating cyclohexene comprising the steps of: (a) separating a mixed solution containing cyclohexene, cyclohexane, and benzene by distillation using N,N-dimethylacetamide as an extractant; and (b) feeding at least a portion of a first bottom liquid obtained by separating cyclohexene, cyclohexane, and benzene from the mixed solution in the step (a) to an extractant purification column, withdrawing an azeotrope of cyclohexyl acetate and N,N-dimethylacetamide from a top of the extractant purification column to an outside of a system, and recycling a second bottom liquid of the extractant purification column to the step (a).

6 Claims, 6 Drawing Sheets

METHOD FOR SEPARATING AND PRODUCING CYCLOHEXENE

TECHNICAL FIELD

The present invention relates to a method for continuously separating and producing cyclohexene on an industrial scale for a long time, and to a method for producing cyclohexanol using cyclohexene obtained by the method.

BACKGROUND ART

Various methods have been known as methods for producing cyclohexene. Partial hydrogenation of benzene is mentioned as one of them. Partial hydrogenation of benzene is generally performed by introducing hydrogen into a suspension of water and benzene in the presence of a ruthenium catalyst to allow a reaction to occur. A mixture containing water, cyclohexane, cyclohexene, unreacted benzene, and the like is obtained as a result of the reaction. In order to obtain high purity cyclohexene from this mixture, a method for separating cyclohexene from the reaction mixture poses a challenge. Since cyclohexane, cyclohexene, and benzene have close boiling points to each other, it is difficult to obtain high purity cyclohexene by the conventional distillation method. For this reason, an extractive distillation process using a solvent such as N-methyl-2-pyrrolidone, N,N-dimethylacetamide, adiponitrile, sulfolane, dimethyl malonate, dimethyl succinate, or ethylene glycol is proposed as a method for separating high purity cyclohexene from the above mixture (Patent Documents 1 and 2).

Patent Document 1: Japanese Patent Laid-Open No. 9-169669

Patent Document 2: Japanese Patent Laid-Open No. 9-30994

DISCLOSURE OF THE INVENTION

Problems to be Solved by the Invention

However, when the present inventor performed extractive distillation of cyclohexene on an industrial scale for a long time using an extractive distillation process described in the above documents, a concentration of impurities in an extractant increased to such an extent that cannot be ignored, resulting in significant reduction in separation performance. This caused a problem that the thermal load applied to the extractive distillation increased with time; the purity of a product was reduced; and finally exchange of the extractant was needed. As a result, it was impossible to continuously obtain high purity cyclohexene for a long time.

Generally, impurities accumulated in the extractant may include those originally contained in an organic phase (oil phase) to be separated and those produced in the process of extractive distillation. Examples of the former may include toluene, styrene, ethylbenzene, methylcyclohexane, cyclohexanone, xylenes, bicyclohexyl, dicyclohexyl ether, and tarry material. Examples of the latter may include a decomposition product of an extractant such as acetic acid and cyclohexyl acetate and a substance produced by further reaction of the decomposition product. Specifically, when N,N-dimethylacetamide is used as an extractant, acetic acid is produced by the hydrolysis of N,N-dimethylacetamide, and the produced acetic acid further reacts with cyclohexene or cyclohexanol to produce cyclohexyl acetate. Accumulation of these impurities in the extractant does not pose a problem at all in short-time operation since both an inflow into the system and a production within the system are each an extremely small amount. However, a problem occurs that when extractive distillation of cyclohexene is performed on an industrial scale for a long time, separation performance of extractive distillation is reduced, leading to increase in the amount of heat necessary for separation and reduction of the purity of cyclohexene.

A literature (Henan Huagong vol. 8, pp 37-38, 2002) describes that, at the time of separating and purifying cyclohexene, the number and the content of impurities present in a distillation column increase with the lapse of time when N,N-dimethylacetamide which is an extractant stays in the distillation column. However, the above literature does not describe nor suggest the problem that when extractive distillation is performed on an industrial scale for a long time, separation performance of extractive distillation is reduced, leading to increase in the amount of heat necessary for separation and reduction of the purity of cyclohexene, and a solution thereof.

Means for Solving the Problems

As a result of careful investigation of the cause of the reduction in the separation performance, the present inventor has obtained a finding that an impurity, particularly cyclohexyl acetate, is the cause of significant reduction in the separation performance of extractive distillation. Based on this finding, it has been found that the separation performance of extractive distillation is maintained by controlling the concentration of cyclohexyl acetate in a bottom liquid recycled to a distillation separation step within a specific range using an extractant purifying column, and as a result high purity cyclohexene can be continuously separated and produced on an industrial scale for a long time.

Specifically, the present invention provides the following.

[1] A method for separating cyclohexene comprising the steps of:

(a) separating a mixed solution containing cyclohexene, cyclohexane, and benzene by distillation using N,N-dimethylacetamide as an extractant; and (b) feeding at least a portion of a first bottom liquid obtained by separating cyclohexene, cyclohexane, and benzene from the mixed solution in the step (a) to an extractant purification column, withdrawing an azeotrope of cyclohexyl acetate and N,N-dimethylacetamide from a top of the extractant purification column to an outside of a system, and recycling a second bottom liquid of the extractant purification column to the step (a) together with a remainder of the first bottom liquid.

[2] The method for separating cyclohexene according to the above [1], wherein a concentration of cyclohexyl acetate in a mixture of the remainder of the first bottom liquid and the second bottom liquid, to be recycled to the step (a), is from 0.5% by weight to 30% by weight.

[3] The method for separating cyclohexene according to the above [1], wherein a concentration of cyclohexyl acetate in a mixture of the remainder of the first bottom liquid and the second bottom liquid, to be recycled to the step (a), is from 1% by weight to 5% by weight.

[4] A method for producing cyclohexene comprising the steps of:

(i) partially hydrogenating benzene to prepare a mixed solution containing cyclohexene, cyclohexane, and benzene;

(ii) separating the mixed solution containing cyclohexene, cyclohexane, and benzene obtained in the step (i) by distillation using N,N-dimethylacetamide as an extractant; and (iii) feeding at least a portion of a first bottom liquid obtained by separating cyclohexene, cyclohexane, and benzene from the mixed solution in the step (ii) to an extractant purification column, withdrawing an azeotrope of cyclohexyl acetate and N,N-dimethylacetamide from a top of the extractant purification column to an outside of a system, and recycling a second bottom liquid of the extractant purification column to the step (ii) together with a remainder of the first bottom liquid.

[5] The method for producing cyclohexene according to the above [4], wherein a concentration of cyclohexyl acetate in a mixture of the remainder of the first bottom liquid and the second bottom liquid, to be recycled to the step (ii), is from 0.5% by weight to 30% by weight.

[6] A method for producing cyclohexanol, comprising hydrating the cyclohexene obtained by the production methods according to the above [4] or [5].

Advantages of the Invention

The separation performance in extractive distillation is maintained by the present invention, and as a result, high purity cyclohexene can be continuously separated and produced on an industrial scale for a long time.

BEST MODE FOR CARRYING OUT THE INVENTION

Hereinafter, the best mode for carrying out the present invention (hereinafter, "the present embodiment") will be described in detail. Note that the present invention is not limited to the following embodiments, but can be modified and implemented in various ways within the scope thereof.

The method for separating cyclohexene according to the present embodiment comprises the steps of: (a) separating a mixed solution containing cyclohexene, cyclohexane, and benzene by distillation using N,N-dimethylacetamide as an extractant; and (b) feeding at least a portion of a first bottom liquid obtained by separating cyclohexene, cyclohexane, and benzene from the mixed solution in the step (a) to an extractant purification column, withdrawing an azeotrope of cyclohexyl acetate and N,N-dimethylacetamide from a top of the extractant purification column to an outside of a system, and recycling a second bottom liquid of the extractant purification column to the step (a) together with a remainder of the first bottom liquid.

[Step (a)]

The step (a) is a step of separating a mixed solution containing cyclohexene, cyclohexane, and benzene by distillation using N,N-dimethylacetamide as an extractant.

In the step (a), there is used a distillation column having a number of theoretical plates of preferably 10 or more, more preferably 20 or more. Generally, N,N-dimethylacetamide which is an extractant is fed to an upper part of the distillation column, and the mixed solution is fed to a lower side than a middle part of the distillation column. An amount of the extractant used is usually equal or more to an amount of the mixed solution, and a reflux ratio is generally from 1 to 20.

[Step (b)]

The step (b) is a step of feeding at least a portion of a first bottom liquid obtained by separating cyclohexene, cyclohexane, and benzene from the mixed solution in the step (a) to an extractant purification column, withdrawing an azeotrope of cyclohexyl acetate and N,N-dimethylacetamide from a top of the extractant purification column to an outside of a system, and recycling a second bottom liquid of the extractant purification column to the step (a) together with a remainder of the first bottom liquid.

Here, the remainder of the first bottom liquid means a remaining portion of the first bottom liquid which has not been fed to the extractant purification column.

The present inventor has collected vapor-liquid equilibrium data or the cyclohexane-cyclohexene system and the cyclohexene-benzene system. As a result, it has been found that when extractive distillation of a multicomponent system is performed by using N,N-dimethylacetamide as an extractant, the relative volatility shows a specific behavior with the concentration of cyclohexyl acetate (refer to FIGS. 4 and 5).

From the vapor-liquid equilibrium data for the cyclohexane-cyclohexene system, it has been found that, in a case where the concentration of cyclohexyl acetate with regard to N,N-dimethylacetamide is 0.5% by weight, the relative volatility of cyclohexane to cyclohexene is larger than that in a case where cyclohexyl acetate is not substantially contained (0% by weight). That is, it has been found that when a small amount of cyclohexyl acetate is present in the extractant, the relative volatility of cyclohexane to cyclohexene increases, and as a result, cyclohexene can be separated with higher purity.

Further, from the vapor-liquid equilibrium data for the cyclohexene-benzene system, it has been found that, in a case where the concentration of cyclohexyl acetate with regard to N,N-dimethylacetamide is 20% by weight, the relative volatility of cyclohexene to benzene is larger than that in a case where the concentration of cyclohexyl acetate is 35% by weight. That is, it has been found that when the concentration of cyclohexyl acetate in the extractant is too high, the relative volatility of cyclohexene to benzene decreases, and as a result, the purity of cyclohexene is reduced.

In the present embodiments, from the results as described above, the concentration of cyclohexyl acetate in the bottom liquid to be recycled to the step (a) is controlled in a range of preferably from 0.5% by weight to 30% by weight, more preferably from 1% by weight to 5% by weight. When the concentration of cyclohexyl acetate is 0.5% by weight or more, the relative volatility of cyclohexane to cyclohexene increases, and cyclohexene tends to be separated with higher purity from the mixed solution. When the concentration of cyclohexyl acetate is 30% by weight or less, the relative volatility of benzene to cyclohexene increases, and cyclohexene tends to be separated with higher purity from the mixed solution. Therefore, by controlling the concentration of cyclohexyl acetate in the bottom liquid to be recycled within the range as described above, the separation performance of extractive distillation is maintained also when the distillation is continuously operated for a long time, and increase in the amount of heat necessary for separation can also be suppressed. Here, the cyclohexyl acetate concentration in the bottom liquid to be recycled to the step (a) is a value measured by gas chromatography.

In the present embodiment, a distillation separation method is used as a method of controlling the concentration of cyclohexyl acetate in the bottom liquid to be recycled to the step (a) because operation is simple and construction of the process is also easy. The purification of the extractant by distillation may be performed continuously or intermittently.

Specifically, it is possible to control the concentration of cyclohexyl acetate in the bottom liquid to be recycled to the step (a) within a range as described above by feeding at least a portion of a bottom liquid obtained by separating the mixed solution containing cyclohexene, cyclohexane, and benzene by distillation in the step (a) to an extractant purification column and withdrawing an azeotrope of cyclohexyl acetate and N,N-dimethylacetamide from the top of the column to the outside of the system.

An embodiment of the present invention will be specifically described below with reference to drawings, but the present invention is not: limited to such an embodiment. FIG. 1 shows an example of a process of separating a mixed solution containing cyclohexane, cyclohexene, and benzene prepared by partial hydrogenation of benzene by distillation using a three-column system.

The mixed solution containing cyclohexane, cyclohexene, and benzene separated from a reaction mixture after partial hydrogenation of benzene is introduced into a middle plate of a distillation column D1 through a line 1. On the other hand, N,N-dimethylacetamide is introduced into an upper part of the distillation column D1 as an extractant through a line 2, and distillation separation is performed. A fraction comprising a substance having a lower boiling point than cyclohexene such as cyclohexane as the main component is withdrawn from a top of the distillation column D1 and condensed by a condenser. Then, a portion of the fraction is returned to the distillation column D1 as reflux, and the remainder is withdrawn through a line 3. A fraction comprising benzene, cyclohexene, and the extractant as main components is withdrawn from the bottom of the distillation column D1 and introduced into a distillation column D2 through a line 4. The extractant is introduced from a line 5 if needed, and distillation separation is performed also in the distillation column D2. A fraction comprising cyclohexene as the main component is withdrawn from the top of the column. A portion of the fraction is returned to the distillation column D2 as reflux, and the remainder is withdrawn through a line 6. A fraction comprising benzene and the extractant as main components is withdrawn from the bottom of the distillation column D2 and introduced into a distillation column D3 through a line 7. Benzene and the extractant are separated by distillation in the distillation column D3, and a fraction comprising benzene as the main component is withdrawn from the top of the column and circulated to the partial hydrogenation reaction. The extractant is withdrawn from the bottom of the distillation column D3, and a portion thereof is fed to an extractant purification column 4. Cyclohexyl acetate and N,N-dimethylacetamide are withdrawn from the top of the extractant purification column 4 to the outside of the system. A bottom liquid of the extractant purification column 4 is replenished with N,N-dimethylacetamide corresponding to that withdrawn from the top of the extractant purification column 4 to the outside of the system and combined with the remainder of bottom liquid of the distillation column 3. The resulting mixture is then recycled to the distillation columns 1 and 2.

A four-column system can be employed for the above process as shown in FIG. 2, wherein a mixture of cyclohexene, cyclohexane, and the like is separated from benzene by distillation separation in a distillation column D1, and then benzene is separated from the extractant in a distillation column D2; on the other hand, the mixture of cyclohexene, cyclohexane, and the like is introduced into a distillation column D3 and successively separated by distillation to separate and recover cyclohexane and cyclohexene.

The method for producing cyclohexene according to the present embodiment comprises the steps of: (i) partially hydrogenating benzene to prepare a mixed solution containing cyclohexene, cyclohexane, and benzene; (ii) separating the mixed solution containing cyclohexene, cyclohexane, and benzene obtained in the step (i) by distillation using N,N-dimethylacetamide as an extractant; and (iii) feeding at least a portion of a first bottom liquid obtained by separating cyclohexene, cyclohexane, and benzene from the mixed solution in the step (ii) to an extractant purification column, withdrawing an azeotrope of cyclohexyl acetate and N,N-dimethylacetamide from the top of the extractant purification column to the outside of the system, and recycling a second bottom liquid of the extractant purification column to the step (ii) together with the remainder of the first bottom liquid.

[Step (i)]

The step (i) is a step of partially hydrogenating benzene to prepare a mixed solution containing cyclohexene, cyclohexane, and benzene. The method of hydrogenating benzene is not particularly limited, but for example a method of introducing benzene and hydrogen into a slurry containing a catalyst and water can be used.

The amount of water used for the reaction changes with the reaction modes, but it is preferable to use the amount that the reaction system forms at least two phases, an organic phase (oil phase) comprising a raw material and a product as main components and an aqueous phase comprising water as the main component. Generally, the amount of water is from 0.01 to 10 times by weight, preferably from 0.1 to 5 times by weight of the amount of benzene as a raw material. The amount of water is preferably 0.01 times by weight or more of the amount of benzene from the viewpoint of easily forming a two phase and facilitating oil-water separation to be described below. The amount of water is preferably 10 times by weight or less of the amount of benzene from the volume of a reaction vessel and obtaining good production efficiency. The amount of water to be used is preferably set in the range as described above with regard to the amount of benzene because this amount of water tends to more selectively yield cyclohexene in the above reaction.

A metal salt may be present in the solution for partial hydrogenation reaction of benzene. Examples of the metal salt may include inorganic acid salts such as sulfates, halides, and phosphates of Group 1 metals and Group 2 metals of the Periodic Table, zinc, manganese, cobalt and the like; or organic acid salts such as acetates of these metals. Zinc sulfate and cobalt sulfate are particularly preferred. The amount of the metal salt used is generally from $1\times10^{-5}$ times by weight to 1 time by weight, preferably from $1\times10^{-4}$ times by weight to 0.1 times by weight of the amount of the water in the reaction system.

A ruthenium-based catalyst is generally used as a catalyst for use in the reaction. Specifically, ruthenium metal obtained by reducing various ruthenium compounds is preferred. Examples of the ruthenium compounds may include inorganic acid salts such as halides, nitrates, and sulfates, hydroxides, complex compounds such as ruthenium carbonyl and a ruthenium amine complex, and alkoxides. Halides are preferred, and ruthenium chlorides are more preferred. Examples of the methods of reducing the ruthenium compounds which can be used may include a catalytic reduction process by hydrogen gas and a chemical reduction process by formalin, hydrazine, boron hydride, and the like. Among them, the catalytic reduction process by hydrogen gas is preferred.

The above metal ruthenium may be independently used as the active ingredient of the catalyst, or another metal component may be used as a co-catalyst in combination. Examples of the co-catalyst may include inorganic acid salts such as halides, nitrates, and sulfates, organic acid salts such as acetates, and complex compounds, of zinc, iron, cobalt, manganese, gold, lanthanum, copper, and the like. Among them, zinc compounds are preferred, and zinc sulfate is more preferred. The amount of the co-catalyst used is preferably from 0.01 to 20, more preferably from 0.1 to 10, in terms of the atomic ratio of co-catalyst metals to ruthenium metal atoms.

The catalyst and the co-catalyst may be unsupported or supported. An unsupported catalyst is prepared, for example, by the following method. After obtaining a mixed solution containing ruthenium metal and optionally a co-catalyst component, the solution is subjected to an alkali precipitation method or the like to obtain the unsupported catalyst as a solid, or the solution may be evaporated to dryness in the state of a homogeneous solution.

A method of preparing a supported catalyst comprises supporting ruthenium metal on a carrier such as silica, alumina, silica-alumina, oxides, composite oxides, and hydroxides of zirconium or other metals, and activated carbon. Known methods can be used as the supporting method, and examples thereof may include an ion exchange method, a spray method, an impregnation method, and an evaporation to dryness method. An ion exchange method is preferred. The amount of ruthenium metal supported is generally from 0.001 to 10% by weight, preferably from 0.1 to 5% by weight based on a carrier. A co-catalyst component may be supported simultaneously with ruthenium metal, or may be supported successively. In addition, the selectivity of cyclohexene produced can be further improved by treating the catalyst with water.

The reaction temperature for partially hydrogenating benzene is generally from 50 to 250° C., preferably from 100 to 220° C. The reaction temperature is preferably 250° C. or less from the viewpoint of producing cyclohexene with sufficient selectivity. The reaction temperature is preferably 50° C. or higher from the viewpoint of maintaining the yield of cyclohexene at a high level with a sufficient reaction rate. Further, the pressure in the system during the partial hydrogenation reaction is from 0.1 to 20 MPa, preferably from 0.5 to 10 MPa in terms of hydrogen pressure. The pressure in the system exceeding 20 MPa can be industrially disadvantageous, and a pressure of less than 0.1 MPa can reduce the reaction rate, leading to the reduction in the yield of cyclohexene. As the reaction modes, it is preferable to employ a continuous system using one reaction vessel or two or more reaction vessels.

The reaction mixture after the partial hydrogenation reaction is a mixture of an aqueous phase in which a ruthenium metal catalyst is dispersed and an organic phase (oil phase) containing benzene, cyclohexene, cyclohexane, and the like as the main components. This reaction mixture is introduced, for example, into a settler of an oil separator to separate oil and water. The oil separator may be installed either in the reactor in which the partial hydrogenation reaction has been performed, or outside the reactor. At least a portion of the separated aqueous phase is preferably circulated to the partial hydrogenation reaction system and reused. On the other hand, the oil phase is a mixed solution containing, as the main components, benzene as a raw material, cyclohexene as a product, and cyclohexane and the like as a by-product, and is separated by distillation using N,N-dimethylacetamide as an extractant in the following step (ii).

Step (ii) and Step (iii)

The step (ii) is a step of separating the mixed solution containing cyclohexene, cyclohexane, and benzene obtained in the step (i) by distillation using N,N-dimethylacetamide as an extractant, and the step (iii) is a step of feeding at least a portion of a first bottom liquid obtained by separating cyclohexene, cyclohexane, and benzene from the mixed solution in the step (ii) to an extractant purification column, withdrawing an azeotrope of cyclohexyl acetate and N,N-dimethylacetamide from the top of the extractant purification column to the outside of the system, and recycling a second bottom liquid of the extractant purification column to the step (ii) together with the remainder of the first bottom liquid.

Herein, the step (ii) and the step (iii) correspond to the step (a) and the step (b) in the above method for separating cyclohexene, respectively, and can be operated in the same manner to produce cyclohexene.

[Production of Cyclohexanol]

Next, a method for producing cyclohexanol by hydrating cyclohexene obtained by the production method according to the present embodiment will be described.

The method for producing cyclohexanol by hydrating cyclohexene is not particularly limited. For example, it can be produced by employing a method using a zeolite catalyst.

A crystalline metallosilicate which is a solid acid catalyst used for the hydration reaction of cyclohexene is a crystalline metallosilicate containing at least one metal selected from among aluminum, boron, gallium, titanium, chromium, iron, zinc, phosphorus, vanadium, and copper. For example, there is mentioned an anhydrous oxide whose composition is represented by general formula (1):

$$pM_{2/n}O.xSiO_2.yAl_2O_3.(1-y)Z_2O_w \quad (1)$$

wherein M represent at least one n-valent cation; O represents oxygen; Si represents silicon; Al represents aluminum; Z represents at least one w-valent metal selected from among boron, gallium, titanium, chromium, iron, zinc, phosphorus, vanadium, and copper; n represents an integer of 1 to 6; w represents an integer of 1 to 6; and $0.3 \leqq p \leqq 1.5$, $1 \leqq x \leqq 1000$, and $0 \leqq y \leqq 1$.

In the general formula (1), M represents a cation in the crystalline metallosilicate, preferably a proton or a cation of Group IB, IIA, IIB, IIIA, IIIB, IVB, VB, VIB, VIIB, or VIII metal on the Periodic Table, more preferably a proton. Further, Z represents at least one metal selected from among boron, gallium, titanium, chromium, iron, zinc, phosphorus, vanadium, and copper. These are metals which are taken in the crystal during hydrothermal synthesis of the crystalline metallosilicate and do not come out of the crystalline metallosilicate even at the subsequent ion exchange operation. Particularly preferred among these metals are boron, gallium, titanium, chromium, and iron.

Specific examples of the crystalline metallosilicate catalyst may include crystalline aluminosilicates such as mordenite, faujasite, clinoptilolite, L-form zeolite, chabazite, erionite, ferrierite, and ZSM-type zeolite announced by Mobil Oil Company, crystalline aluminometallosilicates also containing elements other than aluminum such as boron, gallium, titanium, chromium, iron, zinc, phosphorus, vanadium, and copper, and metailosilicates substantially free of aluminum such as gallosilicate and borosilicate.

It is also possible to use AZ-1 (described in Japanese Patent Laid-Open No. 59-128210), TPZ-3 (described in Japanese Patent Laid-Open No. 58-110419), Nu-3 (described in Japanese Patent Laid-Open No. 57-3714), Nu-5 (described in Japanese Patent Laid-Open No. 57-129820), Nu-6 (described in Japanese Patent Laid-Open No. 57-123817), and Nu-10 (described in Japanese Patent Laid-Open No. 57-200218).

The crystalline metallosilicate has a primary particle size of preferably 0.5 μm or less, more preferably 0.1 μm or less, further preferably 0.05 μm or less. The lower limit of the primary particle size is not particularly limited as long as it is within the range where the X-ray diffraction phenomenon of the crystalline metallosilicate is observed. The lower limit is preferably 2 nm or more.

In the hydration reaction of cyclohexene, side reactions such as isomerization and polymerization occur and by-products such as methylcyclopentenes, dicyclohexyl ether, and bicyclohexyl are produced. In order to suppress such side reactions and obtain cyclohexanol with high yield, it is also effective to use as a catalyst, for example, a crystalline aluminosilicate ZSM-5 disclosed in Japanese Patent Publication No. 4-41131. ZSM-5 is a zeolite developed by Mobil Oil Company (refer to U.S. Pat. No. 3,702,886), in which the silica to alumina molar ratio constituting the crystal is 20 or more and which has three-dimensional pores having inlets of 10-membered oxygen-containing rings in the crystal structure.

The reaction temperature for hydrating cyclohexene is preferably from 50 to 300° C. The reaction temperature is preferably 50° C. or higher from the viewpoint of maintaining high yield with a sufficient reaction rate, and is preferably 300° C. or less from the viewpoint of suppressing side reactions.

Further, the pressure for hydrating cyclohexene is not particularly limited, but a pressure allowing both cyclohexene and water as raw materials to maintain a liquid phase is preferred.

The molar ratio of water to cyclohexene as raw materials is not particularly limited, but too much excess of cyclohexene is not preferred from the viewpoint of the conversion of cyclohexene. On the other hand, too much excess of water is not preferred from the viewpoints of separation; purification of produced cyclohexanol, manufacture of equipment with regard to the necessity of enlarging a reactor and a liquid-liquid separator in the post process, maintenance inspection, operation, and the like. Therefore, the molar ratio of cyclohexene to water is preferably in a range of from 0.01 to 100.

Further, the weight ratio of cyclohexene to the catalyst changes with conditions such as reaction temperature, reaction pressure, molar ratio of cyclohexene to water, but generally, the weight of the catalyst is preferably in a range of from 0.005 to 100 based on the weight of cyclohexene fed to the reactor in 1 hour.

The solution after the reaction, from which the catalyst is to be eliminated, is a liquid containing cyclohexanol, cyclohexene, and a small amount of crystalline metallosilicates which is obtained from the oil phase removed from the liquid-liquid separator after the above catalytic hydration reaction, or a liquid obtained by concentrating the liquid. The concentration of cyclohexanol in the oil phase removed from the liquid-liquid separator is about 12% by weight. A method for industrially obtaining cyclohexanol as a product generally comprises concentrating and purifying cyclohexanol by the operation such as distillation obtain a product, recovering and recycling unreacted cyclohexene, and separating and removing impurities such as a high-boiling substance.

EXAMPLES

Hereinafter, the present embodiment will be described in more detail with reference to Examples. Note that in the following description, "%" refers to "% by mass".

[Measurement of the Concentration of Cyclohexyl Acetate]

About 200 ml of the liquid in the line 2 was withdrawn, and a portion thereof was analyzed by gas chromatography. A gas chromatograph GC-14A and a data processing device CR-5A manufactured by Shimadzu Corporation were used as the analyzer. A packed column (Thermon 1000) was used as a column of the gas chromatograph, and helium gas was passed as a carrier gas. The temperature in a constant temperature bath was set at 70° C., and then increased to 200° C. at a speed of 10° C./min, 15 minutes after pouring 1 μL of the liquid in the line 2. After the temperature is increased, the constant temperature at 200° C. was maintained for 15 minutes to complete the analysis.

Example 1

[Partial Hydrogenation Reaction of Benzene]

Step (i)

Ruthenium particulate which is the hydrogenation catalyst described in Japanese Patent Laid-Open No. 10-279508 as a catalyst was mixed with water 560 times the particulate in terms of the weight ratio, and further mixed with zirconia 5 times the weight of the hydrogenation catalyst and zinc sulfate heptahydrate ($ZnSO_4.7H_2O$) 98 times the weight of the hydrogenation catalyst, thereby forming a slurry. The partial hydrogenation reactor was pressurized with hydrogen gas so that the reaction pressure may be 50 $kg/cm^2G$ at a reaction temperature of 140° C. and the number of stirrer revolutions of 108 rpm. Thereto was fed 0.3 parts by weight of benzene per hour based on 1 part by weight of the slurried catalyst and also was fed hydrogen so as to maintain the reaction pressure of 50 $kg/cm^2G$. The continuous partial hydrogenation reaction of benzene was performed in this way, and the liquid from the exit of the partial hydrogenation reactor was dehydrated in a dehydration column, thereby obtaining a mixed solution containing 51.0% by weight of benzene, 39.2% by weight of cyclohexene, and 9.7% by weight of cyclohexane. The concentration of water in the mixed solution was 2 ppm by weight.

[Distillation Separation of Cyclohexene 1 (Refer to FIG. 1)]

Step (a) and Step (ii)

The distillation separation was performed by feeding 1 part by weight of the mixed solution to the 30th plate (the condenser and the reboiler are also regarded as one plate, respectively, hereafter the same) from the top of the distillation column 1 having the number of theoretical plates of 60, feeding 8 parts by weight of N,N-dimethylacetamide to the fifth plate from the top as an extractant, and controlling the thermal load of the reboiler so that 0.098 parts by weight of cyclohexane having a purity of 98.6% by weight can be distilled from the top of the distillation column 1. The distillation separation was performed by feeding the bottom liquid of the distillation column 1 to the 25th plate from the top of the distillation column 2 having the number of theoretical plates of 50, feeding N,N-dimethylacetamide to the fifth plate from the top as an extractant, and controlling the thermal load of the reboiler so that 0.392 parts by weight of cyclohexene having a purity of 99.7% by weight can be distilled from the top of the distillation column 2. The bottom liquid of the distillation column 2 was fed to the 10th plate from the top of the distillation column 3 having the number of theoretical plates of 20; the thermal load of the reboiler was controlled so that 0.510 parts by weight of benzene having a purity of 99.8% by weight can be distilled from the top of the distillation column 3; and a portion of the distilled benzene was recycled to the partial hydrogenation reaction.

Step (b) and Step (iii)

A portion of the bottom liquid of the distillation column 3 in an amount of 0.08 parts by weight was fed to the 8th plate from the top of the distillation column 4 having the number of theoretical plates of 18; the thermal load of the reboiler was controlled so that the liquid composition at the top of the column was 15% by weight of cyclohexyl acetate and 85% by weight of N,N-dimethylacetamide; and the distillate was withdrawn to the outside of the system. The bottom liquid of the extractant purification column 4 was replenished with N,N-dimethylacetamide corresponding to that withdrawn from the top of the extractant purification column 4 to the outside of the system through a line 8 and combined with the remainder of bottom liquid of the distillation column 3. A predetermined amount of the resulting mixture was then recycled to the distillation columns 1 and 2, respectively.

Table 1 shows the reboiler thermal load of each distillation column, the purity of cyclohexane, the concentration of cyclohexyl acetate in the bottom liquid recycled to the distillation column D1, at 74 hours, 500 hours, 1000 hours, and 10,000 hours after starting operation. An increase in the concentration of cyclohexyl acetate after the lapse of 1000 to 10,000 hours was not observed, and an increase in the reboiler thermal load after the lapse of 0 to 10,000 hours was not observed, either.

Comparative Example 1

Extractive distillation of cyclohexene was performed in the same manner as in Example 1 except that extractant purification column 4 was not used. Table 1 shows the reboiler thermal load of each distillation column, the purity of cyclohexane, cyclohexene, and benzene at the top of the column, and the concentration of cyclohexyl acetate in the bottom liquid recycled to the distillation column D1, at 100 hours, 1000 hours, 2400 hours, 4000 hours, 6000 hours, 7000 hours, and 8000 hours after starting operation. The reboiler thermal load after the lapse of 100 to 2400 hours was equivalent to those in Example 1, but the reboiler thermal load increased after the lapse of more than 2400 hours. Further, after the lapse of 8000 hours, it was impossible to maintain the purity of the cyclohexene in the top liquid of the distillation column D2 at a level equivalent to that in Example 1.

FIG. 6 shows the relation between the concentration of cyclohexyl acetate in the line 2 and the reboiler thermal load. These results show that the reboiler thermal load (particularly the thermal load of the distillation column D2) significantly increases when the concentration of cyclohexyl acetate in the line 2 is higher than 30% by weight.

was obtained without performing dehydration operation. The concentration of water in the mixed solution was 120 ppm by weight.

[Distillation Separation of Cyclohexene 2 (Refer to FIG. 2)]
Step (a) and Step (ii)

The distillation separation was performed by feeding 1 part by weight of the mixed solution to the 27th plate (the condenser and the reboiler are also regarded as one plate, respectively, hereafter the same) from the top of the distillation column D1 having the number of theoretical plates of 50, feeding 8 parts by weight of N,N-dimethylacetamide to the second plate from the top as an extractant, and controlling the thermal load of the reboiler so that 0.510 parts by weight of a mixed liquid containing 4% by weight of N,N-dimethylacetamide, 0.19% by weight of benzene, 19.01% by weight of cyclohexane, and 76.61% by weight of cyclohexene can be distilled from the top of the distillation column D1. The distillation separation was performed by feeding the bottom liquid of the distillation column D1 to the 9th plate from the top of the distillation column 2 having the number of theoretical plates of 20 and controlling the thermal load of the reboiler so that 0.510 parts by weight of benzene having a purity of 99.8% by weight can be distilled from the top of the distillation column D2. A portion of the resulting benzene was recycled to the reaction system. A portion of the bottom liquid of the distillation column D2 was fed to the extractant purification column D5, and the remainder was replenished with the extractant, from the bottom liquid of the distillation column 4, in an amount corresponding to that withdrawn from the top of the distillation column D1. Then, a predetermined amount of the resulting liquid was recycled to the distillation column D1.

Next, 0.510 parts by weight of a distillate from the top of the distillation column D1 was fed to the 30th plate from the top of the distillation column D3 having the number of theoretical plates of 60. The distillation separation was performed by feeding 8 parts by weight of N,N-dimethylacetamide to the fifth plate from the top as an extractant and controlling the thermal load of the reboiler so that 0.098 parts by weight of cyclohexane having a purity of 98.6% by weight can be distilled from the top of the distillation column D3. The distillation separation was performed by feeding the bottom

TABLE 1

| | | | Distillation column D1 | | Distillation column D2 | | Distillation column D3 | | Extractant purification column D4 | D1-D4 |
|---|---|---|---|---|---|---|---|---|---|---|
| | Operation time [Hr] | Line 2 ① [wt %] | Qr [$10^3$ kJ/Hr] | ② [wt %] | Qr [$10^3$ kJ/Hr] | ③ [wt %] | Qr [$10^3$ kJ/Hr] | ④ [wt %] | Qr [$10^3$ kJ/Hr] | Qr total [$10^3$ kJ/Hr] |
| Example 1 | 74 | 0.1 | 1340 | 98.6 | 477 | 99.7 | 1,010 | 98.6 | 80 | 2,907 |
| | 500 | 0.6 | 1205 | 98.6 | 480 | 99.7 | 1,010 | 98.6 | 51 | 2,746 |
| | 1,000 | 1 | 1208 | 98.6 | 478 | 99.7 | 1,009 | 98.6 | 39 | 2,734 |
| | 10,000 | 0.9 | 1210 | 98.6 | 476 | 99.7 | 1,012 | 98.6 | 40 | 2,738 |
| Comparative | 100 | 0.1 | 1320 | 98.6 | 475 | 99.7 | 1034 | 98.6 | 0 | 2,829 |
| Example 1 | 1000 | 1.3 | 1210 | 98.6 | 476 | 99.7 | 1035 | 98.6 | 0 | 2,721 |
| | 2400 | 4.5 | 1220 | 98.6 | 480 | 99.7 | 1036 | 98.6 | 0 | 2,736 |
| | 4000 | 10.3 | 1350 | 98.6 | 485 | 99.7 | 1036 | 98.6 | 0 | 2,871 |
| | 6000 | 21 | 1510 | 98.6 | 490 | 99.7 | 1030 | 98.6 | 0 | 3,030 |
| | 7000 | 28 | 1630 | 98.6 | 510 | 99.7 | 1032 | 98.6 | 0 | 3,172 |
| | 8,000 | 35 | 1830 | 98.6 | 1250 | 97.1 | 1035 | 98.6 | 0 | 4,115 |

Qr Reboiler thermal load
① Concentration of cyclohexyl acetate in line 2 (wt %)
② Purity of cyclohexane at the top of the column (wt %)
③ Purity of cyclohexene at the top of the column (wt %)
④ Purity of benzene at the top of the column (wt %)

Example 2

[Partial Hydrogenation Reaction of Benzene]
Step (i)

The partial hydrogenation reaction of benzene was performed in the same manner as in Example 1, and a mixed solution containing 51.0% by weight of benzene, 39.2% by weight of cyclohexene, and 9.7% by weight of cyclohexane liquid of the distillation column D3 to the 10th plate from the top of the distillation column D4 having the number of theoretical plates of 20 and controlling the thermal load of the reboiler so that 0.392 parts by weight of cyclohexene having a purity of 99.7% by weight can be distilled from the top of the distillation column D4.

Step (b) and Step (iii)

A portion of the bottom liquid of the distillation column D4 in an amount of 0.03 parts by weight was fed to the 8th plate from the top of the distillation column D5 having the number of theoretical plates of 18 together with 0.05 parts by weight of a withdrawn portion of the bottom liquid of the distillation column 2; the reflux ratio was controlled so that the liquid composition at the top of the extractant purification column D5 was 15% by weight of cyclohexyl acetate and 85% by weight of N,N-dimethylacetamide; and the distillate was withdrawn to the outside of the system. The bottom liquid of the extractant purification column D5 was replenished with N,N-dimethylacetamide corresponding to that withdrawn from the top of the extractant purification column D5 to the outside of the system through a line 8 and then combined with the bottom liquid of the distillation column D5. The resulting mixture was recycled to the distillation columns D1.

Table 2 shows the reboiler thermal load of each distillation column, the purity of cyclohexane, cyclohexene, and benzene at the top of the column, and the concentration of cyclohexyl acetate in the bottom liquid recycled to the distillation column D1, at 74 hours, 1000 hours, and 10,000 hours after starting operation. An increase in the concentration of cyclohexyl acetate after the lapse of 1000 to 10,000 hours was not observed, and an increase in the reboiler thermal load after the lapse of 0 to 10,000 hours was not observed, either.

Comparative Example 2

Extractive distillation of cyclohexene was performed in the same manner as in Example 2 except that extractant purification column 5 was not used. Table 2 shows the reboiler thermal load of each distillation column, the purity of cyclohexane, cyclohexene, and benzene at the top of the column, and the concentration of cyclohexyl acetate in the bottom liquid recycled to the distillation column D1, at 50 hours, 320 hours, and 540 hours after starting operation. The reboiler thermal load and the concentration of cyclohexyl acetate in the bottom liquid recycled to the distillation column D1 after the lapse of 50 hours was equivalent to those in Example 2, but it was observed that the reboiler thermal load and the concentration of cyclohexyl acetate increased after the lapse of more than 320 hours. Further, after the lapse of more than 540 hours, the continuous operation was impossible because the distillation column D1 began to show signs of flooding, and it was impossible to maintain the purity of cyclohexene and cyclohexane in the top liquid of the distillation columns D1 and D4 at a level equivalent to those in Example 2.

Reference Example 1

The same operation as in Example 2 was performed except that cyclohexyl acetate was separated and removed in the extractant purification column 5 so that the concentration of cyclohexyl acetate in the extractant recycled to the distillation column D1 is less than 0.5% by weight. Table 2 shows the reboiler thermal load of each distillation column, the purity of cyclohexane, cyclohexene, and benzene at the top of the column, and the concentration of cyclohexyl acetate in the bottom liquid recycled to the distillation column D1, at 50 hours and 500 hours after starting operation. In order to maintain the concentration of cyclohexyl acetate fed to the distillation column D1 at less than 0.5% by weight, the amount of the bottom liquids D2 and D4 fed to the extractant purification column 5 need to be increased from 0.08 parts by weight in Example 2 to 0.24 parts by weight, and the reboiler thermal load of the distillation column D5 also increased. On the other hand, the reboiler thermal load of the distillation column D1 was slightly lower than those after 1000 hours and 10,000 hours in Example 2, but the reboiler thermal load of the distillation column D3 was higher than those after 1000 hours and 10,000 in Example 2.

TABLE 2

| | | | Distillation column D1 | | Distillation column D2 | | Distillation column D3 | | Distillatio column D4 | | Extractant purification column D5 | D1-D5 |
|---|---|---|---|---|---|---|---|---|---|---|---|---|
| | Operation time [Hr] | Line 2 ① [wt %] | Qr [$10^3$ kJ/Hr] | ② [wt %] | Qr [$10^3$ kJ/Hr] | ③ [wt %] | Qr [$10^3$ kJ/Hr] | ④ [wt %] | Qr [$10^3$ kJ/Hr] | ⑤ [wt %] | Qr [$10^3$ kJ/Hr] | Qr total [$10^3$ kJ/Hr] |
| Example 2 | 74 | 0.2 | 940 | 99.4 | 477 | 99.8 | 1,290 | 98.6 | 433 | 99.7 | 79 | 3219 |
| | 1,000 | 1.2 | 956 | 99.4 | 478 | 99.8 | 1,109 | 98.6 | 429 | 99.7 | 59 | 3031 |
| | 10,000 | 1.1 | 956 | 99.4 | 476 | 99.8 | 1,112 | 98.6 | 433 | 99.7 | 60 | 3037 |
| Comparative | 50 | 0.3 | 945 | 99.4 | 475 | 99.8 | 1,200 | 98.6 | 431 | 99.7 | 0 | 3051 |
| Example 2 | 320 | 15 | 1010 | 99.4 | 490 | 99,8 | 1,250 | 98.6 | 432 | 99.7 | 0 | 3182 |
| | 540 | 41 | 1,530 | 99 | 490 | 99.8 | 1,321 | 98.6 | 435 | 99.3 | 0 | 3776 |
| Reference | 50 | 0.4 | 945 | 99.4 | 475 | 99.8 | 1,250 | 98.6 | 430 | 99.7 | 625 | 3725 |
| Example 1 | 500 | 0.39 | 944 | 99.4 | 476 | 99.8 | 1,260 | 98.6 | 431 | 99.7 | 630 | 3741 |

Qr Reboiler thermal load

① Concentration of cyclohexyl acetate (wt %)

② (cyclohexane + cyclohexene)/(cyclohexane + cyclohexene + benzene) × 100 at the top of the column (wt %)

③ Purity of benzene at the top of the column (wt %)

④ Purity of cyclohexane at the top of the column (wt %)

⑤ Purity of cyclohexene at the top of the column (wt %)

[Production of Cyclohexanol (Refer to FIG. 3)]

In the production of cyclohexanol, the ZSM-5 particulate which is the crystalline aluminosilicate described in Japanese Patent Laid-Open No. 3-193622 was used as a crystalline metallosilicate which is a catalyst. This crystalline aluminosilicate had a primary particle size of 0.1 μm. This crystalline aluminosilicate was mixed with twice its weight of water to obtain a slurried catalyst. The gas phase portion of a reactor 1 was pressurized with nitrogen gas so that the reaction pressure may be 6 kg/cm$^2$ at a reaction temperature of 125° C. and a number of stirrer revolutions of 530 rpm. Cyclohexene obtained from the top of the distillation column 2 in Example 1 by distillation was fed in an amount of 1 part by weight per hour based on 1 part by weight of the catalyst, and water in an amount corresponding to the amount of water consumed in the reaction was fed through a raw material feed pipe 7. The amount of the slurried catalyst recycled to the reactor 1 via a return pipe 9 was controlled so that the oil water interface level of in a separator 2 was located lower than an exhaust pipe 10. The liquid fed via the exhaust pipe 10 to a distillation column 3 was a cyclohexene mixed solution containing 11.8% by weight of cyclohexanol. The liquid withdrawn from the top of the distillation column 3 was recycled to the reactor 1 via an exhaust pipe 11. The composition of the liquid was a cyclohexene mixed solution containing 0.23% by weight of cyclohexanol. The liquid obtained from the bottom of the distillation column 3 was a cyclohexanol mixed solution containing 30% by weight of cyclohexene. This bottom liquid in an amount of 100 parts by weight was fed to a filter 4 via an exhaust pipe 12. The pressure of the feed liquid was set at a pressure higher than the filtrate side pressure by 1 kg/cm$^2$G, and the filtrate was obtained by this filtration differential pressure. The obtained filtrate was fed to a distillation column 5 via an exhaust pipe 14, and the residual liquid was recycled to the reactor 1 as a filtration circulation liquid via an exhaust pipe 13. Unreacted cyclohexene was recovered from the top of the distillation column 5 via an exhaust pipe 15 and recycled to the reactor 1. High-boiling impurities produced in a trace amount in the reactor 1 were withdrawn from the bottom via an exhaust pipe 17 to the outside of the system. High purity cyclohexanol was thus obtained from a product withdrawing pipe 16 which was provided at a position lower than the connection part of the exhaust pipe 14 and the distillation column 5 and higher than the bottom of the column.

INDUSTRIAL APPLICABILITY

According to the present invention, the separation performance in extractive distillation is maintained by controlling the concentration of cyclohexyl acetate in the bottom liquid to be recycled to the distillation separation step within a specific range, and as a result, an increase in the amount of heat used for distillation and loss of an extractant can be suppressed, and high purity cyclohexene can be continuously separated and produced for a long time.

Figure 1:
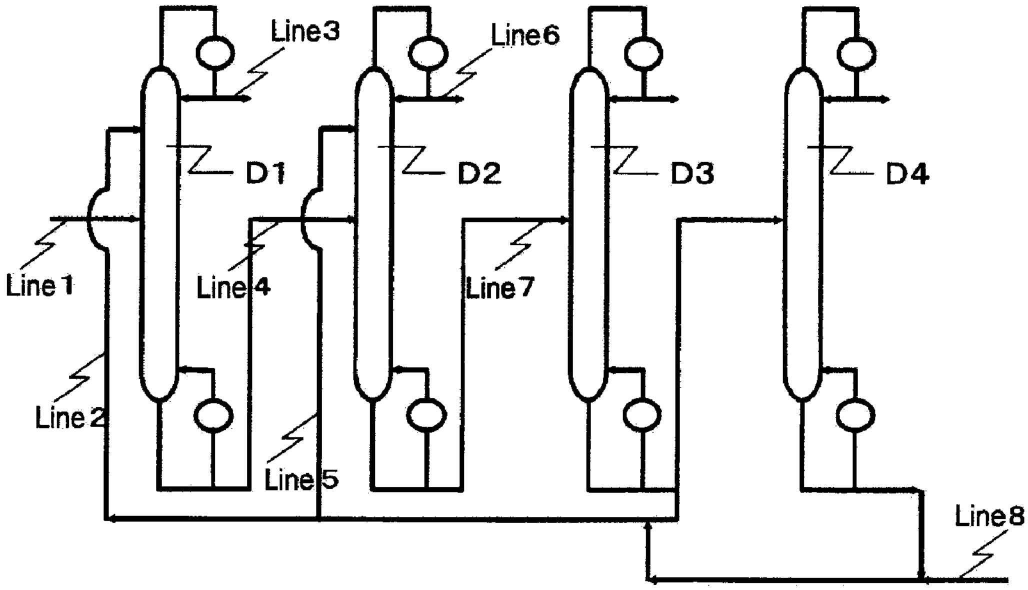
FIG. 1 is a flowchart showing one example of the extractive distillation system of the present invention (D1 . . . First distillation column; D2 . . . Second distillation column; D3 . . . Third distillation column; D4 Extractant purification column).
Figure 2:
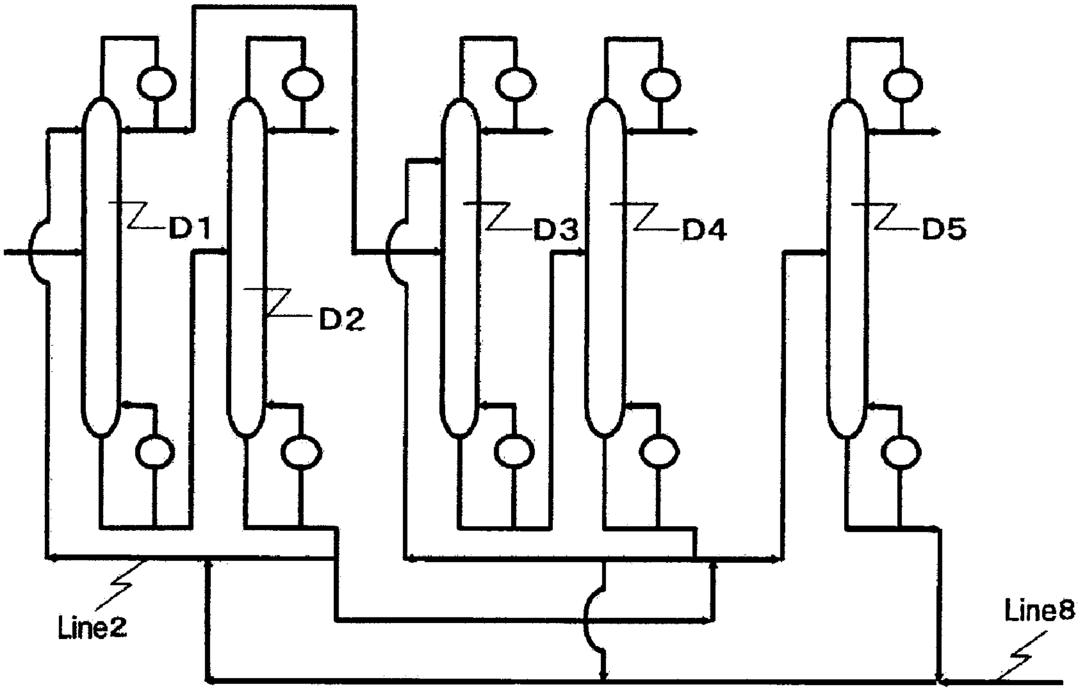
FIG. 2 is a flowchart showing one example of the extractive distillation system of the present invention (D1 . . . First distillation column; D2 . . . Second distillation column; D3 . . . Third distillation column; D4 . . . Fourth distillation column; D5 Extractant purification column).
Figure 3:
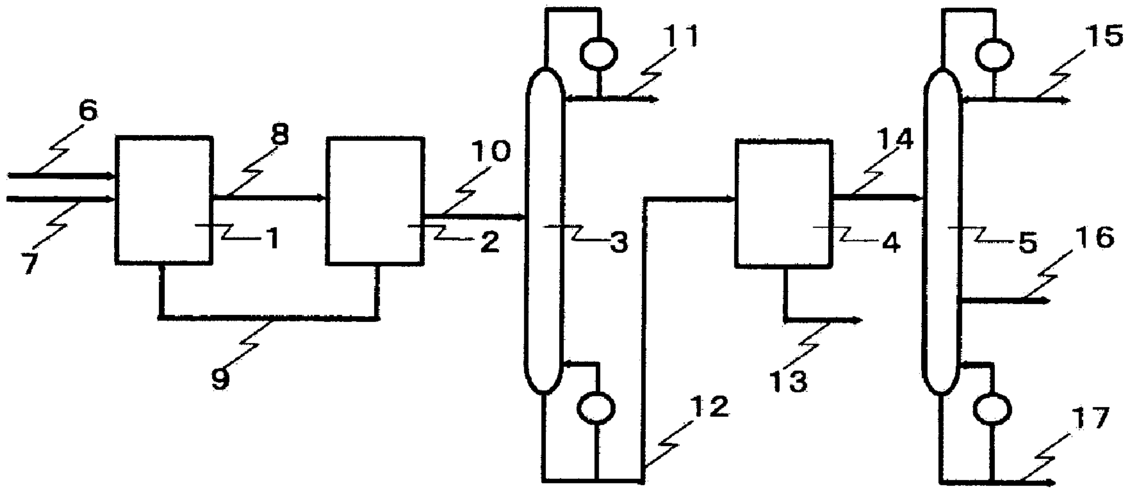
FIG. 3 is a flowchart showing one example of the hydration process flow sheet in the production of cyclohexanol of the present invention (1 . . . Reactor; 2 . . . Separator; 3 . . . Distillation column; 4 . . . Filter; 5 . . . Distillation column; 6 . . . Raw material feed pipe; 7 . . . Raw material feed pipe; 8 . . . Exhaust pipe; 9 . . . Return pipe; 10, 11, 12, 13, 14, 15 . . . Exhaust pipe; 16 . . . Product withdrawing pipe; 17 . . . Exhaust pipe).
Figure 4:
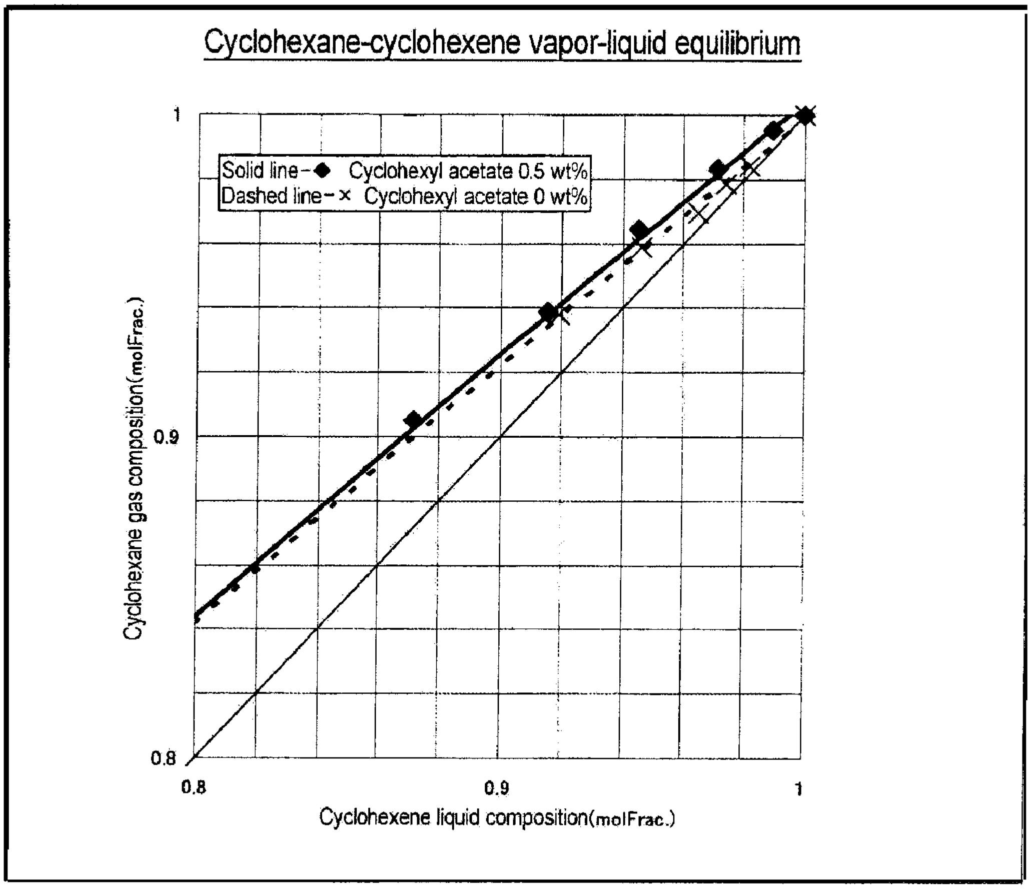
FIG. 4 shows the relation between the concentration of cyclohexyl acetate in N,N-dimethylacetamide and the relative volatility of cyclohexane-cyclohexene.
Figure 5:
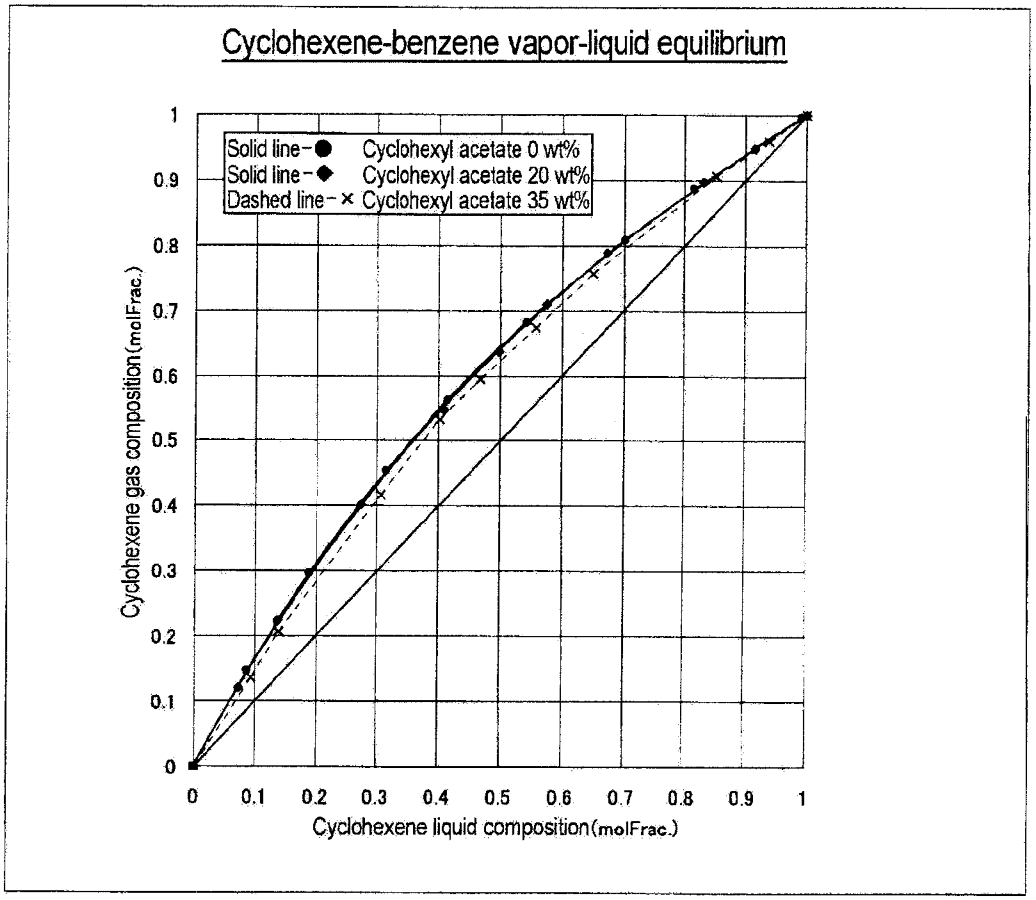
FIG. 5 shows the relation between the concentration of cyclohexyl acetate in N,N-dimethylacetamide and the relative volatility of cyclohexene-benzene.
Figure 6:
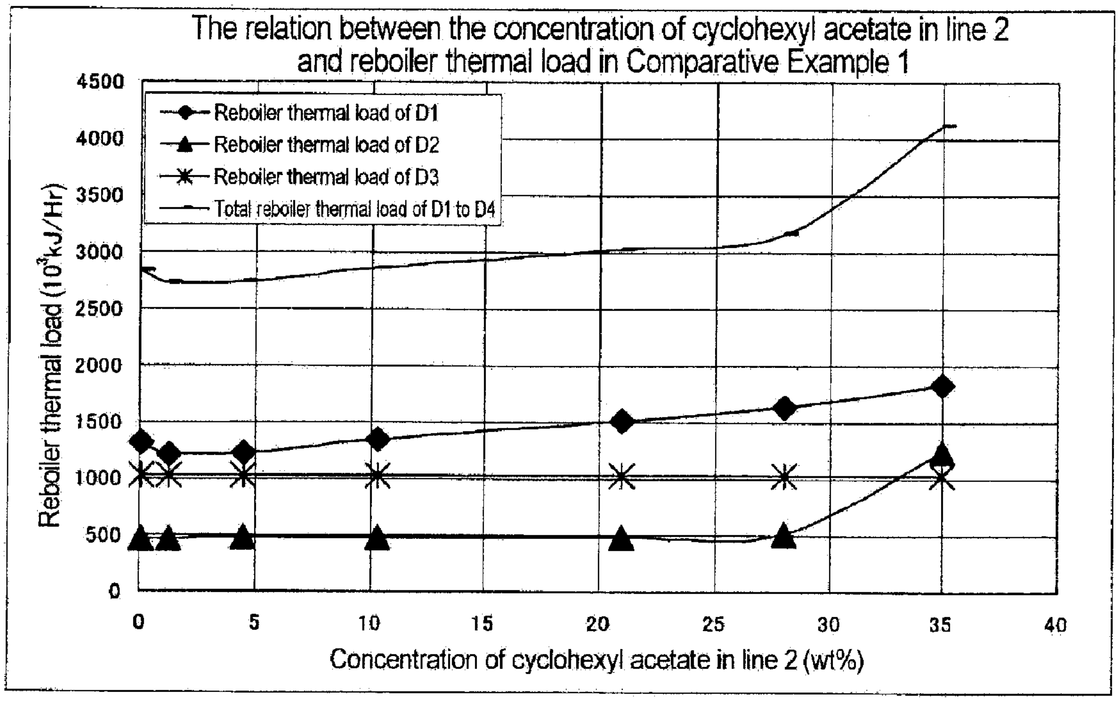
FIG. 6 shows the relation between the concentration of cyclohexyl acetate in line 2 and the reboiler thermal load.

The invention claimed is:

1. A method for separating cyclohexene comprising the steps of:

(a) separating a mixed solution containing cyclohexene, cyclohexane, and benzene by distillation using N,N-dimethylacetamide as an extractant; and (b) feeding at least a portion of a first bottom liquid obtained by separating cyclohexene, cyclohexane, and benzene from the mixed solution in the step (a) to an extractant purification column, withdrawing an azeotrope of cyclohexyl acetate and N,N-dimethylacetamide from a top of the extractant purification column to an outside of a system, and recycling a second bottom liquid of the extractant purification column to the step (a) together with a remainder of the first bottom liquid.

2. The method for separating cyclohexene according to claim 1, wherein a concentration of cyclohexyl acetate in a mixture of the remainder of the first bottom liquid and the second bottom liquid, to be recycled to the step (a), is from 0.5% by weight to 30% by weight.

3. The method for separating cyclohexene according to claim 1, wherein a concentration of cyclohexyl acetate in a mixture of the remainder of the first bottom liquid and the second bottom liquid, to be recycled to the step (a), is from 1% by weight to 5% by weight.

4. A method for producing cyclohexene comprising the steps of:

(i) partially hydrogenating benzene to prepare a mixed solution containing cyclohexene, cyclohexane, and benzene;

(ii) separating the mixed solution containing cyclohexene, cyclohexane, and benzene obtained in the step (i) by distillation using N,N-dimethylacetamide as an extractant; and (iii) feeding at least a portion of a first bottom liquid obtained by separating cyclohexene, cyclohexane, and benzene from the mixed solution in the step (ii) to an extractant purification column, withdrawing an azeotrope of cyclohexyl acetate and N,N-dimethylacetamide from a top of the extractant purification column to an outside of a system, and recycling a second bottom liquid of the extractant purification column to the step (ii) together with a remainder of the first bottom liquid.

5. The method for producing cyclohexene according to claim 4, wherein a concentration of cyclohexyl acetate in a mixture of the remainder of the first bottom liquid and the second bottom liquid, to be recycled to the step (ii), is from 0.5% by weight to 30% by weight.

6. A method for producing cyclohexanol, comprising hydrating the cyclohexene obtained by the production methods according to claim 4 or 5.

* * * * *